United States Patent
Welsh

(10) Patent No.: US 9,413,961 B2
(45) Date of Patent: Aug. 9, 2016

(54) ARTICULATING DISPLAY AND CONTROL MONITOR DEVICE FOR A MOBILE RADIOGRAPHIC MACHINE

(71) Applicant: Thomas Welsh, Aurora, IL (US)

(72) Inventor: Thomas Welsh, Aurora, IL (US)

(73) Assignee: SWISSRAY ASIA HEALTHCARE CO., LTD., Taipei (TW)

( * ) Notice: Subject to any disclaimer, the term of this patent is extended or adjusted under 35 U.S.C. 154(b) by 111 days.

(21) Appl. No.: 14/476,706

(22) Filed: Sep. 3, 2014

(65) Prior Publication Data

US 2015/0350545 A1 Dec. 3, 2015

Related U.S. Application Data

(60) Provisional application No. 61/873,247, filed on Sep. 3, 2013.

(51) Int. Cl.
| | |
|---|---|
| *H04N 9/47* | (2006.01) |
| *H04N 7/18* | (2006.01) |
| *H04N 5/232* | (2006.01) |
| *A61B 6/00* | (2006.01) |
| *A61B 6/03* | (2006.01) |
| *G06F 3/041* | (2006.01) |

(52) U.S. Cl.
CPC ............ *H04N 5/23245* (2013.01); *A61B 6/035* (2013.01); *A61B 6/4405* (2013.01); *A61B 6/462* (2013.01); *A61B 6/468* (2013.01); *G06F 3/0412* (2013.01); *H04N 7/181* (2013.01)

(58) Field of Classification Search
None
See application file for complete search history.

(56) References Cited

U.S. PATENT DOCUMENTS

| | | | |
|---|---|---|---|
| 8,493,323 B2* | 7/2013 | Griffin | G06F 1/1626 345/158 |
| 2014/0140589 A1* | 5/2014 | Klotzer | G06F 19/321 382/128 |
| 2014/0143298 A1* | 5/2014 | Klotzer | H04L 67/2823 709/203 |
| 2015/0049862 A1* | 2/2015 | Ancar | A61B 6/08 378/190 |
| 2016/0073978 A1* | 3/2016 | Henderson | A61B 6/0457 5/600 |

\* cited by examiner

*Primary Examiner* — Frederick Bailey
*Assistant Examiner* — Talha M Nawaz
(74) *Attorney, Agent, or Firm* — Leong C. Lei

(57) ABSTRACT

An articulating display and control monitor device is disclosed. The articulating display and control monitor device a base mobile radiographic machine may include a display monitor coupled to a monitor arm and a video device with a selected one of a video camera and a web cam, the video device provides a video stream from an area in front of the mobile radiographic machine to assist a user transporting the mobile radiographic machine as the video stream is displayed on the display monitor. The display monitor utilizes a video streaming drive mode only when the monitor arm is docked, the display monitor is utilized in conjunction with the articulating display and control monitor device only when the monitor arm is undocked, the monitor arm docks only when the articulating display and control monitor device is docked.

20 Claims, 17 Drawing Sheets

ARTICULATING DISPLAY AND CONTROL MONITOR DEVICE FOR A MOBILE RADIOGRAPHIC MACHINE

This application claims priority to U.S. Provisional Application 61/873,247 filed on Sep. 3, 2013, the entire disclosure of which is incorporated by reference.

BACKGROUND OF THE INVENTION

1. Field of the Invention

The present invention is an articulating display and control monitor device. More specifically, the present invention is an articulating display and control monitor device for a mobile radiographic machine.

2. Description of the Related Art

The medical industry has introduced many various devices, techniques, and methods to perform non-invasive examinations to view inside a patient's body. Among these are radiographic or X-Ray images, computer axial tomography or CAT scans, and ultrasonic images. It is common for the medical industry to introduce devices that are developed specifically to be mobile, whereby they may be moved to a patient, rather than requiring the patient to be moved to the device. It is always the goal to create an image for the medical expert to quickly diagnose the patient. Images may be merely viewed, or may be preserved by capture and storage. Digital images may be enhanced, filtered, improved, compared, and shared utilizing digital software.

Many medical devices in use today use display monitors that are interactive, meaning that the technician has both the display and touch-screen computer control functions. The medical technician must have accessible and safe control of the mobile medical device, and assist or oversee the patient to assure that acceptable images are attained.

Typically, these machines incorporate all of the same devices that are required in a non-mobile digital radiographic machine, namely a device to generate an X-Ray beam, another device to capture the radiographic image, mechanical structural mechanism to position the beam source and image collector, and electronic systems to power and control the beam source and read, process, and enhance the collected digital images. Additional complexity is required to add mobility to this system. It is mandatory that the mechanical positioning mechanism provide a means to compact the overall machine size for wheeled mobile "Transport Mode". Ease and safety of maneuver is important. The simplest mobile DR machines use a folding design that is mounted on casters. The DR machine is manually folded, moved, and plugged into the building AC power outlet for operation. The high-end mobile DR machines are much heavier and provide an electrical motorized drive system to assist the technician in "Transport Mode". A re-chargeable battery power system is used to power the drive wheels and optionally the DR devices.

What is really needed is an improved visual access, control, and safety for mobile digital radiographic or DR machines by providing an articulating display and control monitor. Improvements are realized both during parked "Diagnostic Use Mode" and mobile "Transport Mode", with docking and lock-out features to prevent inadvertent misuse in either use mode, or when switching between these modes.

BRIEF SUMMARY OF THE INVENTION

The present invention is an articulating display and control monitor device. More specifically, the present invention is an articulating display and control monitor device for a mobile radiographic machine.

The articulating display and control monitor device for a mobile radiographic machine includes a display monitor coupled to a monitor arm, the monitor arm coupled to a rotational pivot device, the rotational pivot device coupled to a top of a mobile radiographic machine column, the display monitor rotates about a vertical axis extending from the mobile radiographic machine thereby allowing the display monitor to rotate around the mobile radiographic machine column, the display monitor is utilized by the mobile radiographic machine only when the monitor arm is undocked and the monitor arm undocks only when the articulating display and control monitor device is undocked. The articulating display and control monitor device also includes a video device with a selected one of a video camera and a web cam, the video device provides a video stream from an area in front of the mobile radiographic machine to assist a user transporting the mobile radiographic machine as the video stream is displayed on the display monitor, the display monitor utilizes a video streaming drive mode only when the monitor arm is docked, the display monitor is utilized in conjunction with the articulating display and control monitor device only when the monitor arm is undocked, the monitor arm docks only when the articulating display and control monitor device is docked, the monitor arm is undocked unless until the mobile radiographic machine is already docked and the mobile radiographic machine monitor may not be undocked until the monitor arm is undocked.

It is an object of the present invention to provide an articulating display and control monitor device for a mobile radiographic machine that provides improved control access and visibility to the technician during "diagnostic use mode" by providing a movable and adjustable monitor.

It is an object of the present invention to provide an articulating display and control monitor device for a mobile radiographic machine where docking and locking of the articulating monitor and the DR arm are functionally linked.

It is an object of the present invention to provide an articulating display and control monitor device for a mobile radiographic machine that includes a DR arm that may not be undocked while the articulating monitor is docked.

It is an object of the present invention to provide an articulating display and control monitor device for a mobile radiographic machine that includes an articulating monitor that automatically locks as it docks.

It is an object of the present invention to provide an articulating display and control monitor device for a mobile radiographic machine that includes an articulating monitor display that switches when the articulating monitor is docked.

It is an object of the present invention to provide an articulating display and control monitor device for a mobile radiographic machine that includes a video display that is provided on the docked Articulating Monitor to assist the technician driving the mobile DR machine in "Transport Mode".

It is an object of the present invention to provide an articulating display and control monitor device for a mobile radiographic machine that may be an accessory or replacement of the DR machine monitor.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention however the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
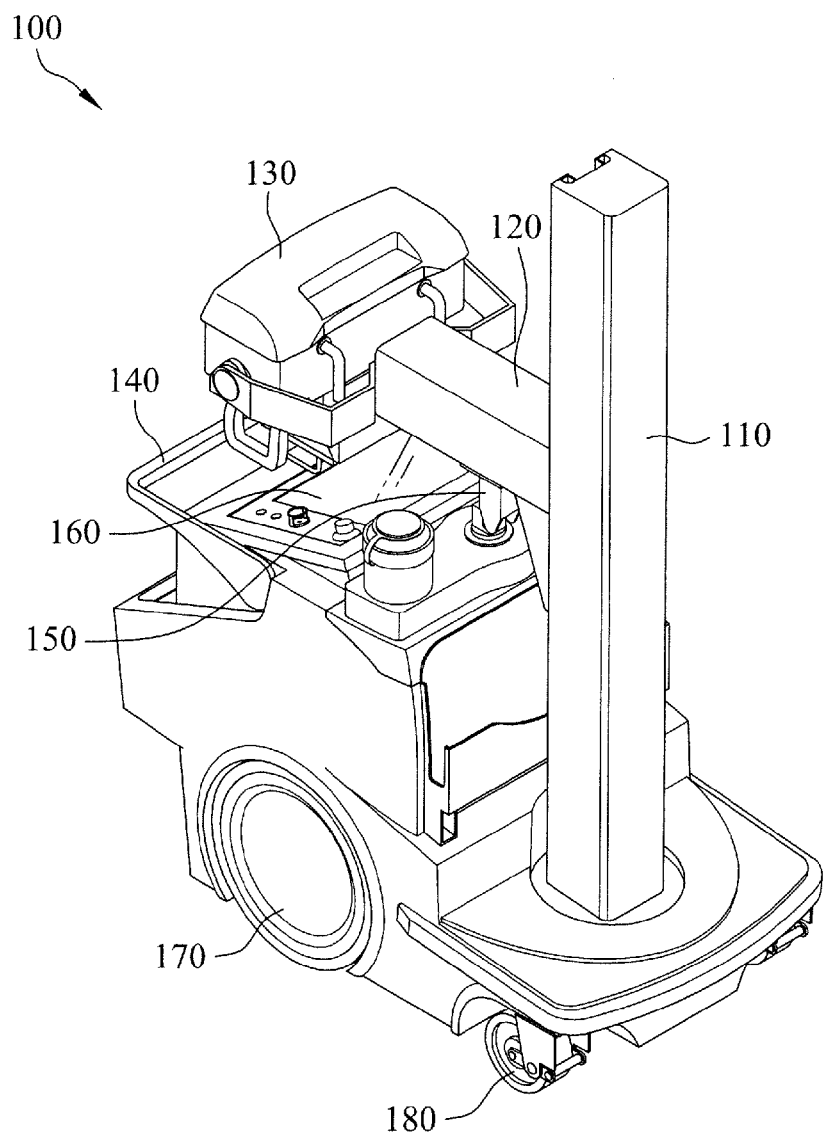
FIG. 1 illustrates a side view of a mobile radiographic machine in transportation mode, in accordance with one embodiment of the present invention.

FIG. 1 illustrates a side view of a mobile radiographic machine 100 in transportation mode, in accordance with one embodiment of the present invention.

The mobile radiographic machine 100 may include a mobile radiographic machine column 110, a horizontal DR arm 120, an X-ray beam source 130, a drive control handle 140, a docking lock 150, a touch screen monitor 160, a motorized rear drive wheel 170 and a front caster 180.

The mobile radiographic machine described herein was developed for an industry leading high-end mobile DR machine. This machine uses an articulating vertical column and horizontal arm system to support and position the X-Ray beam source. The DR arm is mounted to a trolley device integrated to the column to allow vertical rolling. The column is mounted to a rotational pivot device integrated to the machine chassis floor. The DR arm can raise and lower as well as rotate 360 degrees about the column vertical axis. The unit is mobile by means of electric motorized rear wheels and front casters. The column is located in front and virtually independent of the body of the machine. A touch-screen monitor is located on top of the body of the machine, behind the column, facing upward. The machine is generally not safe to enter "Transport Mode" unless the DR arm supporting the X-Ray tube is docked into a locked position that provides a compact stature that is secured and balanced. There are safety systems that prevent rapid machine movement if the DR arm is not properly docked and locked. The docking places the DR arm and X-Ray beam source over the monitor. The operator has tactile hand control by means of the drive control handle to control the pace and steering motions while walking behind the machine. The visibility directly in front of the DR machine is limited and partially obstructed. The upward facing monitor under the DR arm and X-Ray beam source is completely obstructed for viewing. This is not an optimal situation for safe driving transport of the DR mobile machine.

Figure 2:
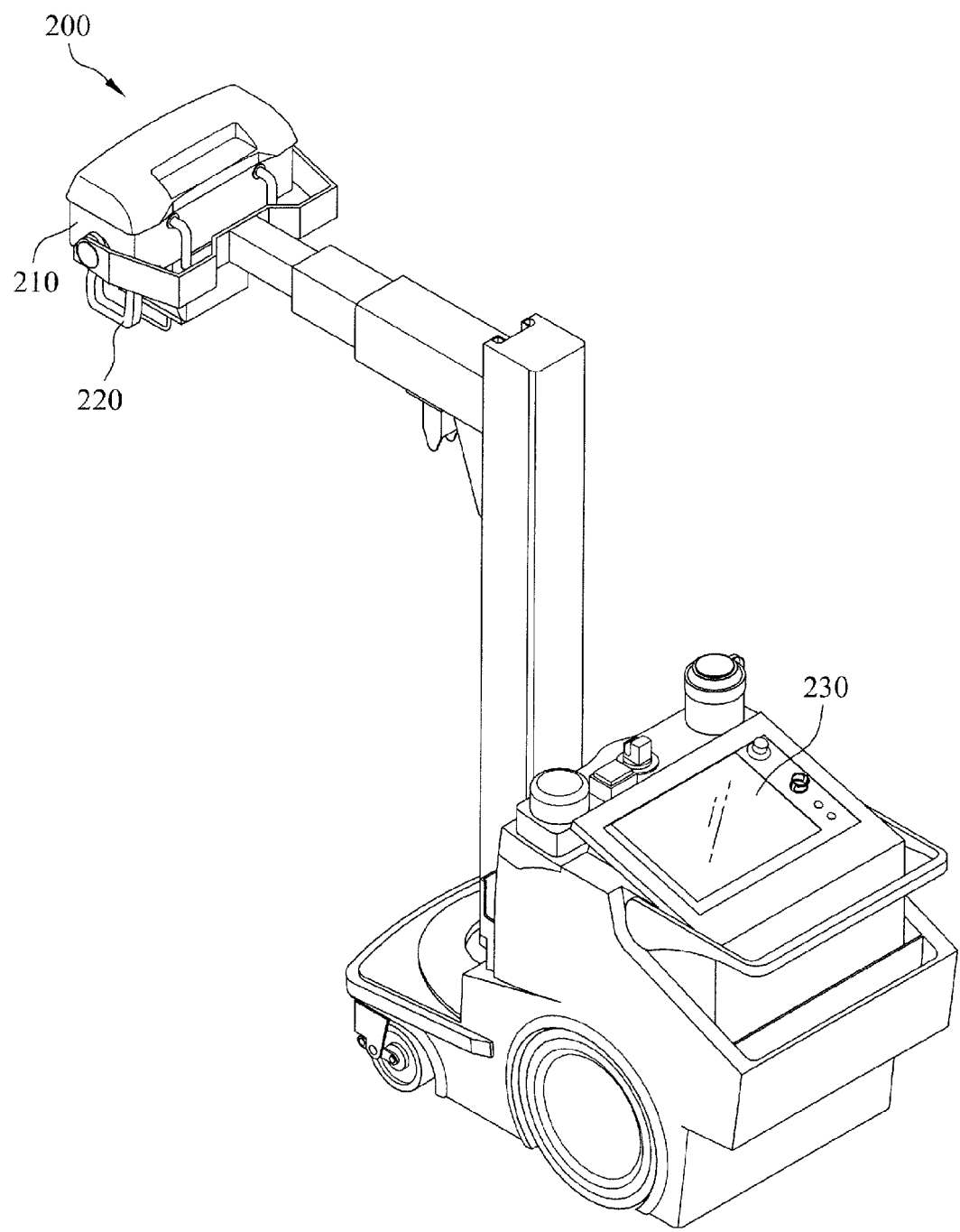
FIG. 2 illustrates a side view of a mobile radiographic machine in diagnostic use mode, in accordance with one embodiment of the present invention.

FIG. 2 illustrates a side view of a mobile radiographic machine 200 in diagnostic use mode, in accordance with one embodiment of the present invention.

The mobile radiographic machine 200 may include an X-ray beam source 210, a pair of DR arm control handles 220 and a DR machine monitor 230.

When it is time to use the mobile radiographic machine for diagnosis, the DR arm must be unlocked, undocked, raised, outwardly extended, and rotated to a useful position. Future mobile DR machines may have these functions motorized and computer driven. Currently, these are manual operations performed by the technician. The DR arm control handles were designed for two handed manipulation of the end of the DR arm while standing facing the end of the DR arm. So the technician that is moving and adjusting the end of the DR arm is a long distance from the DR machine monitor, and cannot easily view the display, or operate the touch-screen controls. The technician must move back closer to the monitor to use it. This is often an iterative process between adjusting the X-Ray beam source, patient, and using the monitor. This is not an optimal situation for efficient diagnostic operation of the mobile DR machine.

Figure 3:
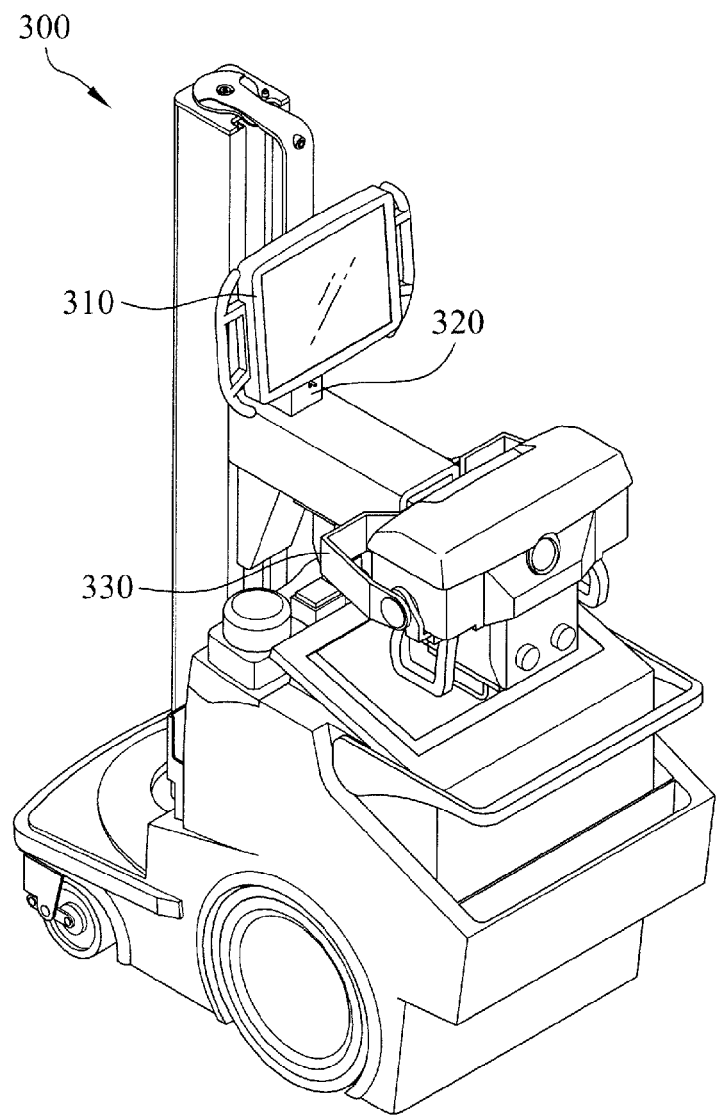
FIG. 3 illustrates a front view of an articulating display and control monitor device, in accordance with one embodiment of the present invention.

FIG. 3 illustrates a front view of an articulating display and control monitor device 300, in accordance with one embodiment of the present invention.

The articulating display and control monitor device 300 may include a monitor arm assembly 310, a monitor dock and lock device 320 and a DR arm dock and lock device 330.

The articulating display and control monitor device described herein provides improvement for both "Diagnostic Use Mode" and "Transport Mode". This articulating display and control monitor device was developed as a second monitor accessory to be added to the mobile DR Machine shown above. However, the articulating display and control monitor device provides the same improvements when it replaces the original monitor. Therefore, this articulating display and control monitor device can be used as accessory or integrated into the overall machine.

The new articulating display and control monitor device is an "Articulating Display and Control Monitor Device for Mobile Radiography Machines". This articulating display and control monitor device may be used as accessory or an integrated improvement to the current "state-of-the-art" machine. This articulating display and control monitor device improves visibility, control, and ease of use in two distinct modes of use. In "Diagnostic Use Mode" the technician has improved access to the touch-screen monitor for visibility and computer control. In "Transport Mode" the technician has a vision system that displays the path in front of the machine by displaying camera video on the rear facing monitor display. The articulating display and control monitor device works in concert with, and improves safety of the existing "Transport Use" docking and locking system of the machine.

Figure 4:
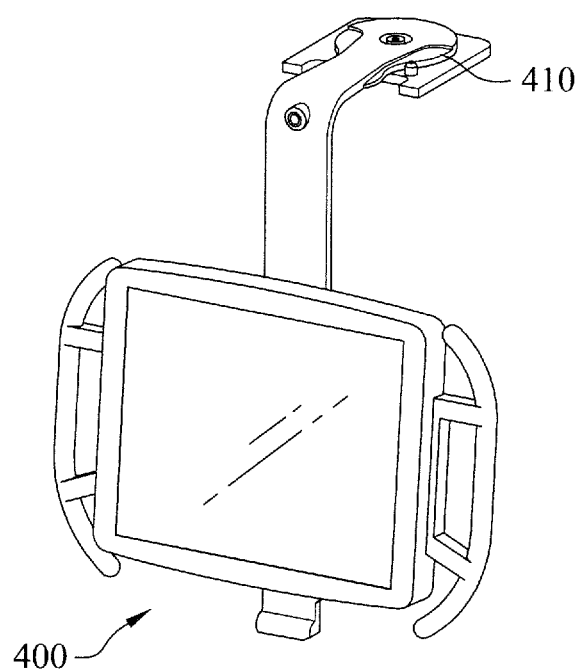
FIG. 4 illustrates a front view of display monitor, in accordance with one embodiment of the present invention.

FIG. 4 illustrates a front view of display monitor 400, in accordance with one embodiment of the present invention.

The display monitor 400 may include a rotational pivot device 410.

Displaying a video to assist a vehicle driver is not a new concept. Likewise, adding a second monitor display to an existing DR machine is not a new concept. What is new and unique about this articulating display and control monitor device is the ability to functionally switch monitor display modes as the DR machine switches between different use modes, and the new articulating display and control monitor device mechanical Dock and Lock system that functions in concert with the DR Arm dock and lock system. The invented device does not limit, constrain, or encumber the full functionality of original DR machine.

Figure 5:
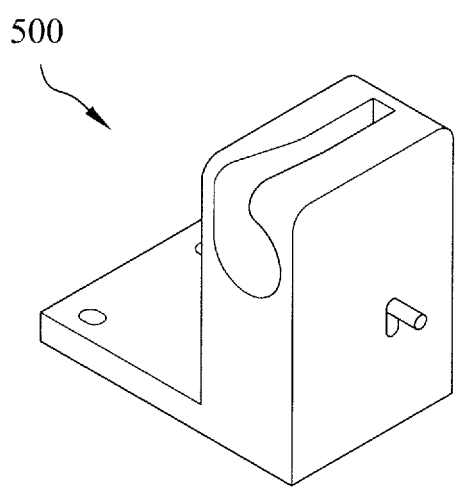
FIG. 5 illustrates a back view of a monitor dock and lock device, in accordance with one embodiment of the present invention.

FIG. 5 illustrates a back view of a monitor dock and lock device 500, in accordance with one embodiment of the present invention.

The articulating display and control monitor device has a Display Monitor mounted on a Monitor Arm. The Monitor Arm is mounted to a Rotational Pivot Device integrated to the top of the DR machine Column. The Display Monitor is able to rotate about a vertical axis thus allowing the Display Monitor to travel around the Column. This rotational freedom is constrained by stops. It is preferable that one of the stops be the dock/lock position which in line with the dock/lock position of the DR Arm. The DR machine also has its own DR Arm Dock & Lock device.

The Articulating Monitor Device is rotationally positioned in the docked and locked position for "Transport Mode". The new Dock & Lock Device is mounted to the top of the DR Arm. This holds and supports the end of the Monitor DR Arm must be properly docked and docked before the Monitor Arm may be docked and locked. When the Monitor Arm is docked and locked, the DR Arm is obstructed from movement.

Figure 6:
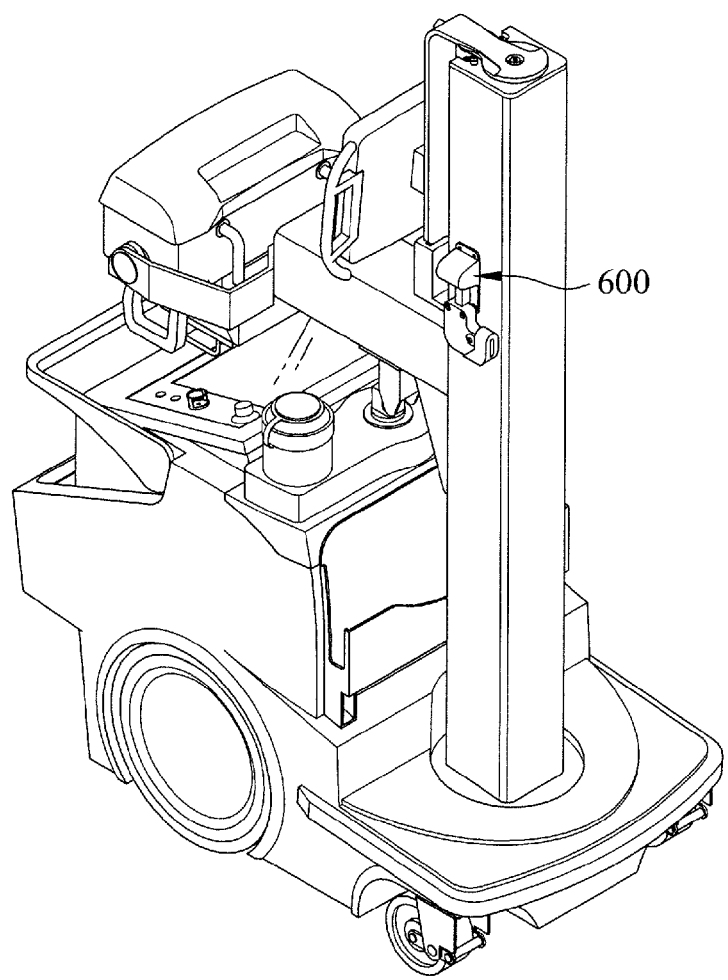
FIG. 6 illustrates a side view of a video device assembly, in accordance with one embodiment of the present invention.

FIG. 6 illustrates a side view of a video device assembly 600, in accordance with one embodiment of the present invention.

The articulating display and control monitor device also uses a Video Device Assembly with a video camera or web cam to view the path in front of the DR Machine. This is used in "Transport Mode" to assist the technician driving the machine as the video is displayed on the docked rear facing Display Monitor.

Figure 7:
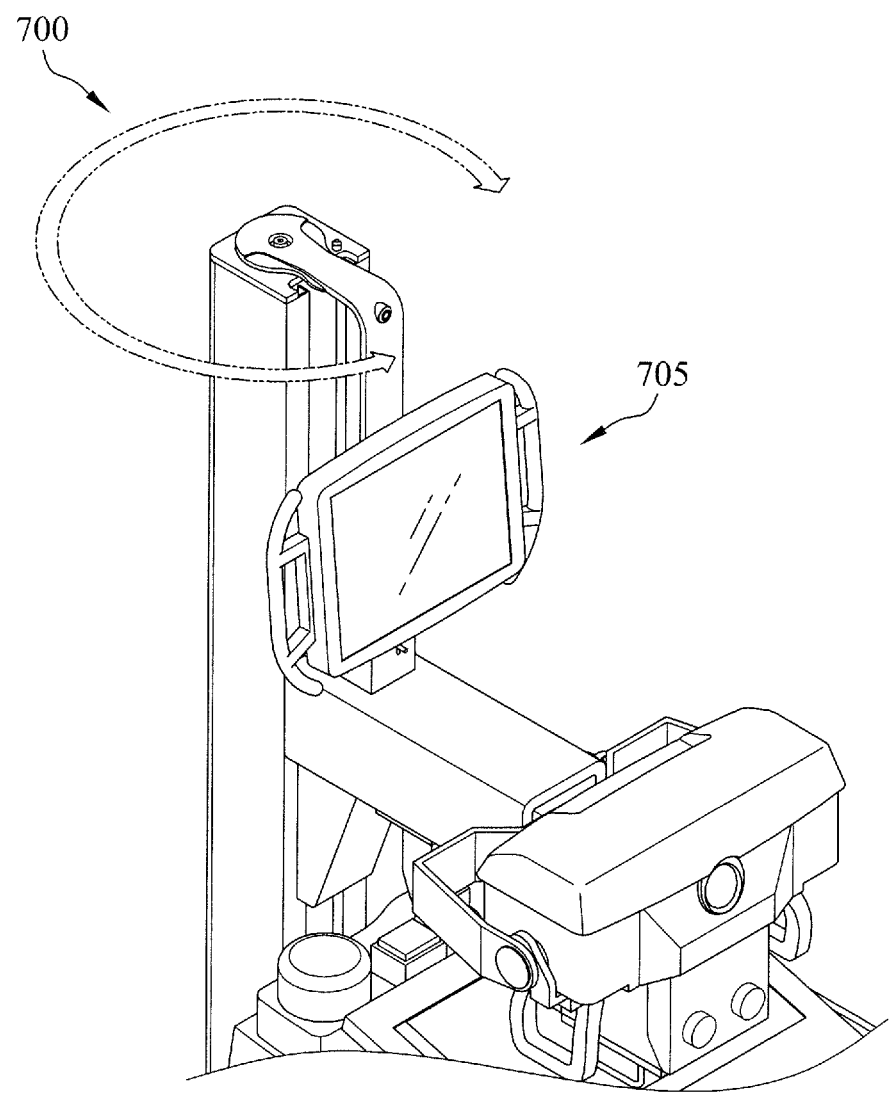
FIG. 7 illustrates a front view of an articulating monitor in a docked position, in accordance with one embodiment of the present invention.

FIG. 7 illustrates a front view of an articulating monitor 700 in a docked position 705, in accordance with one embodiment of the present invention.

Figure 8:
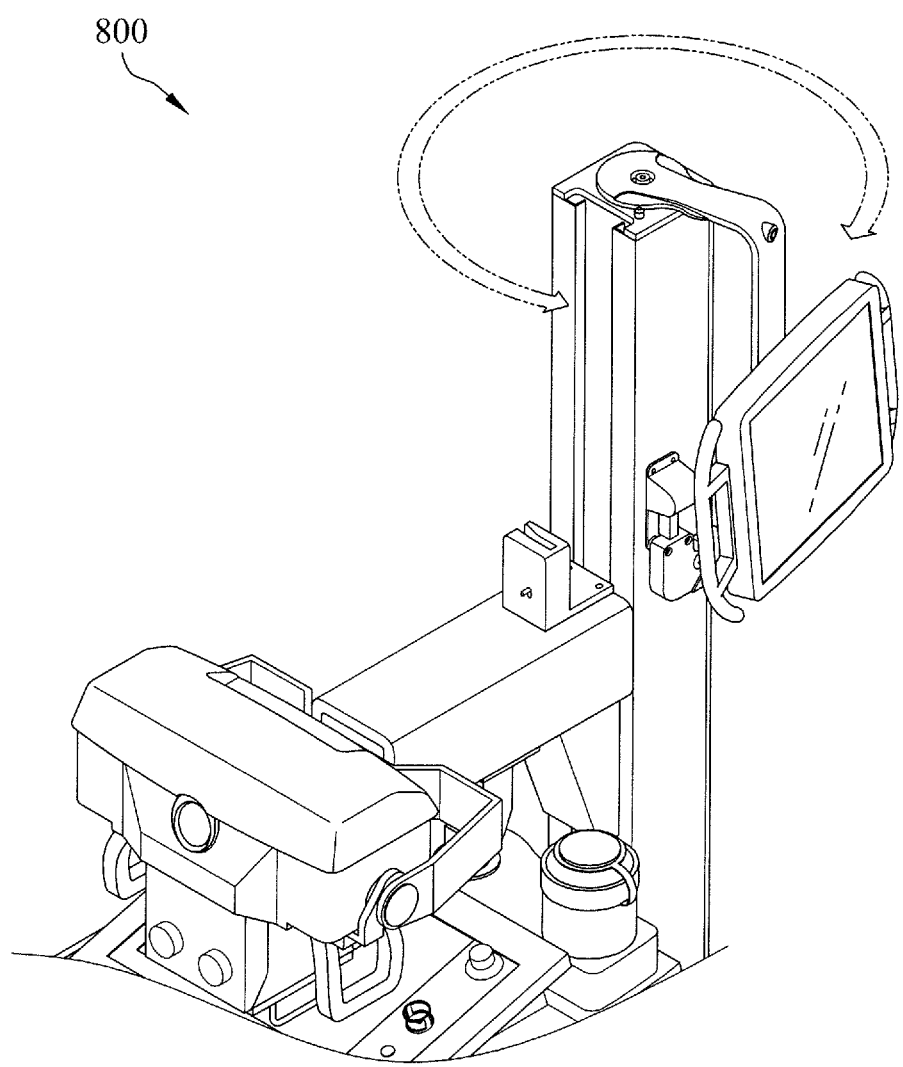
FIG. 8 illustrates a front view of a rotated articulating monitor, in accordance with one embodiment of the present invention.

FIG. 8 illustrates a front view of a rotated articulating monitor 800, in accordance with one embodiment of the present invention.

The images above depict the preferred rotational range and freedom of the Articulating Monitor Arm. The dock/lock position is at one end of an approximate 270 degree range. This rotation range is preferable because the Display Monitor may be positioned on either side of the DR machine, normal to the DR Arm. It is preferable to locate the "Transport Mode" docking at either end of the rotational range to permit one way entry and exit. Another reason is that rotation of the Articulating Monitor is never impeded when the DR Arm is raised up for "Diagnostic Use Mode".

Figure 9:
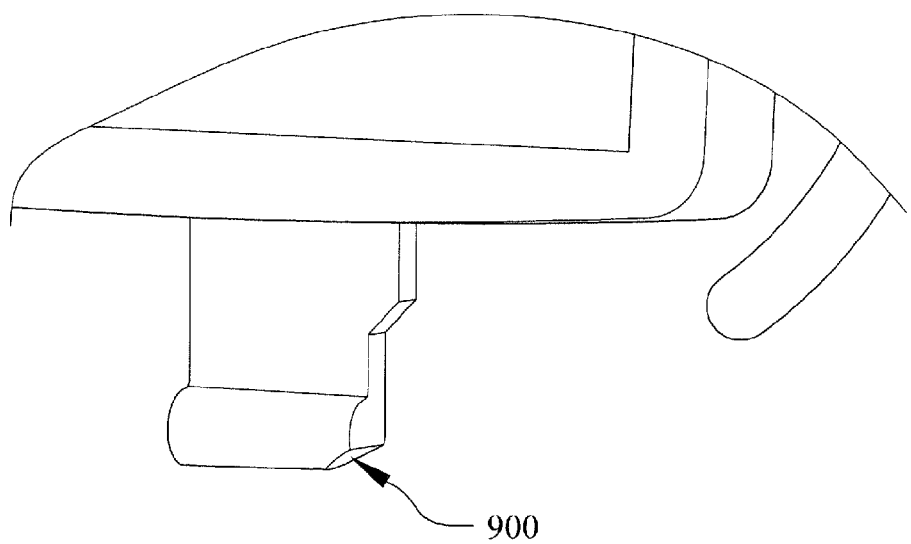
FIG. 9 illustrates a front view of a ramped end, in accordance with one embodiment of the present invention.

FIG. 9 illustrates a front view of a ramped end 900, in accordance with one embodiment of the present invention.

The ramped end 900 may be for automatic lock latch engagement.

The Display Monitor is shown in this disclosure as rigidly fixed to the Monitor Arm. However, additional motion freedom, or additional positioning adjustability, may be incorporated such as pivot, swivel, tilt, and vertical and horizontal translation.

Figure 10:
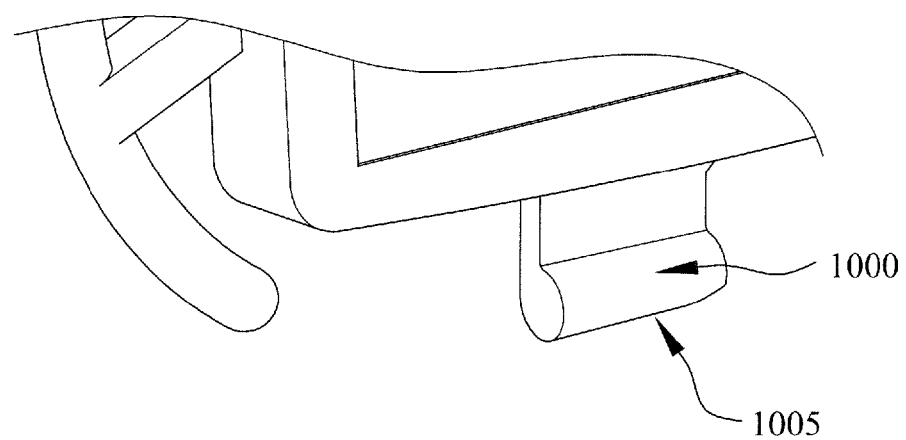
FIG. 10 illustrates a side view of a monitor arm with a male docking geometry, in accordance with one embodiment of the present invention.

FIG. 10 illustrates a side view of a monitor arm 1000 with a male docking geometry 1005, in accordance with one embodiment of the present invention.

Figure 11:
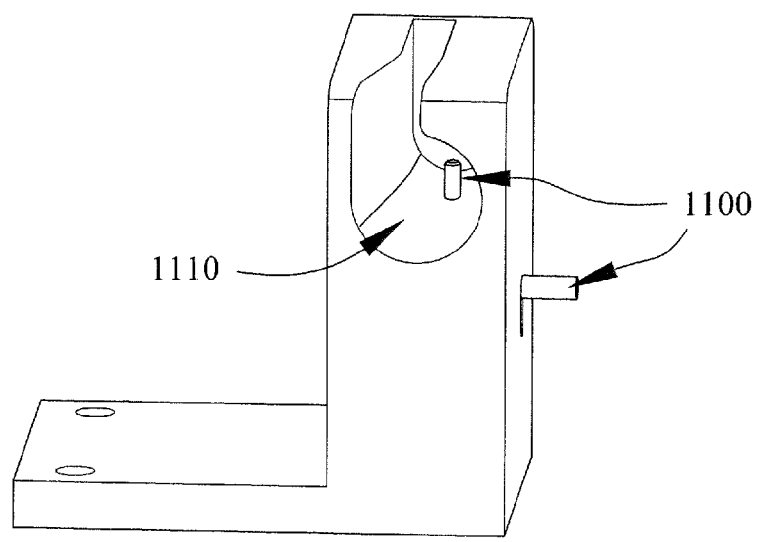
FIG. 11 illustrates a pair of lock latches, in accordance with one embodiment of the present invention.

FIG. 11 illustrates a pair of lock latches 1100, in accordance with one embodiment of the present invention.

The pair of lock latches 1100 may include a monitor lock and lock female geometry 1110.

The Monitor Arm rotates clock-wise out of the Monitor Dock & Lock Device and counterclockwise into said device. The Monitor Dock & Lock Device mounted to the top of the DR Arm has receptacle geometry that rotationally mates the geometry on the DR Arm. The geometry of both entities is rotationally tapered to guide the mating parts to a snug secure resting place as the Monitor Arm rotates into the dock. The design shown has a female geometry on the Dock & Lock Device and a male geometry on the Monitor Arm, however this could be reversed to achieve the same result.

Figure 12:
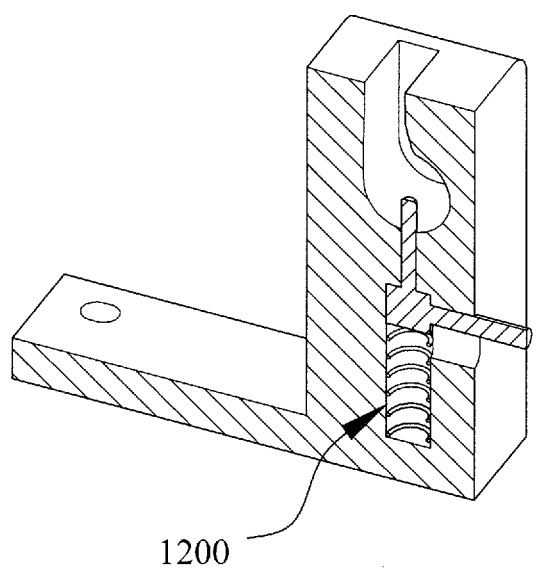
FIG. 12 illustrates a cross-sectional view of a latch spring, in accordance with one embodiment of the present invention.

FIG. 12 illustrates a front view of a latch spring 1200, in accordance with one embodiment of the present invention.

The Lock Latch is designed to engage and lock the Monitor Arm to hold it into the docking position. A Lock Latch is captivated within slotted holes machined into the Block. The Lock Latch has translational freedom to slide from a position where the engagement pin does not enter the docking geometry (unlocked position), to another position that enters the docking geometry (locked position). A directional bias is applied to the Lock Latch to position the Lock Latch in the locked position. There are many design variations to accomplish the result intended for this articulating display and control monitor device which is to provide a locking mechanism that engages automatically when the DR Arm is rotated into the Dock & Lock Device. The Monitor Arm end has a Ramp designed to push the Lock Latch out of the locked position as it enters the Block, then the Latch Spring pushes the Lock Latch into the locked position when the Monitor Arm is fully docked and the Lock Latch may enter the hole in the end of the Monitor Arm. The release of the Monitor Arm for undocking requires the Lock Latch to be pushed down before the Monitor Arm may be rotated out of the Dock & Lock Device.

The Monitor Arm end has a Ramp designed to push the Lock Latch out of the locked position as it enters the Block, then the Latch Spring pushes the Lock Latch into the locked position when the Monitor Arm is fully docked and the Lock Latch may enter the hole in the end of the Monitor Arm. The release of the Monitor Arm for undocking requires the Lock Latch to be pushed down before the Monitor Arm may be rotated out of the Dock & Lock Device.

Figure 13:
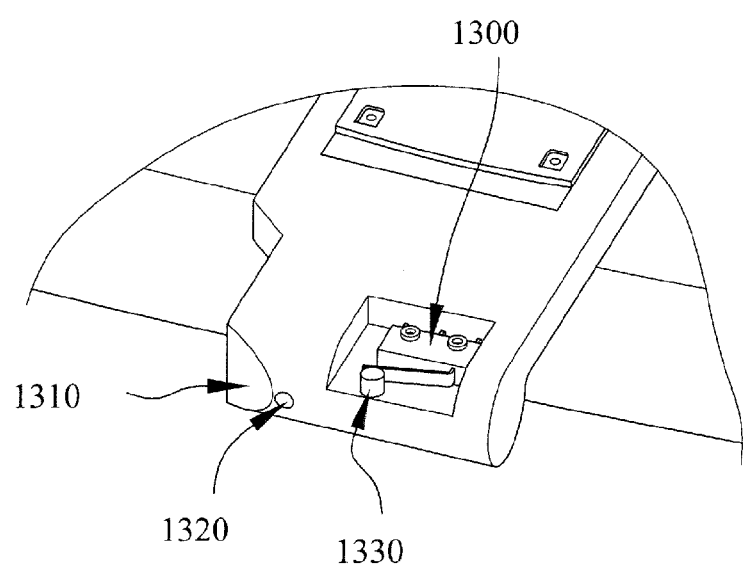
FIG. 13 illustrates a front view of a micro switch, in accordance with one embodiment of the present invention.

FIG. 13 illustrates a front view of a micro switch 1300, in accordance with one embodiment of the present invention.

The micro switch 1300 may include a ramp 1310, a lock latch engagement 1320 and an actuator 1330.

A Micro-Switch is configured such that the circuit is open until the Actuator is depressed, at which time the circuit is closed. The Micro-Switch is positioned such that as the Monitor Arm is docked and locked into the Monitor Dock & Lock Device, the Actuator is depressed and an electronic circuit is closed. This switch configuration is part of the video circuitry such that the Display Monitor only displays the video for "Transport Mode" driving assistance when the Monitor Arm is docked and locked.

When the Micro-Switch is open, the Display Monitor has full display and control features of the original mobile DR Machine Monitor. As an accessory, the second Display Monitor provides two locations where the technician may control the machine and view the images produced. Or mobile DR machines could use only the Articulating Monitor described in this articulating display and control monitor device and eliminate the original monitor.

Figure 14:
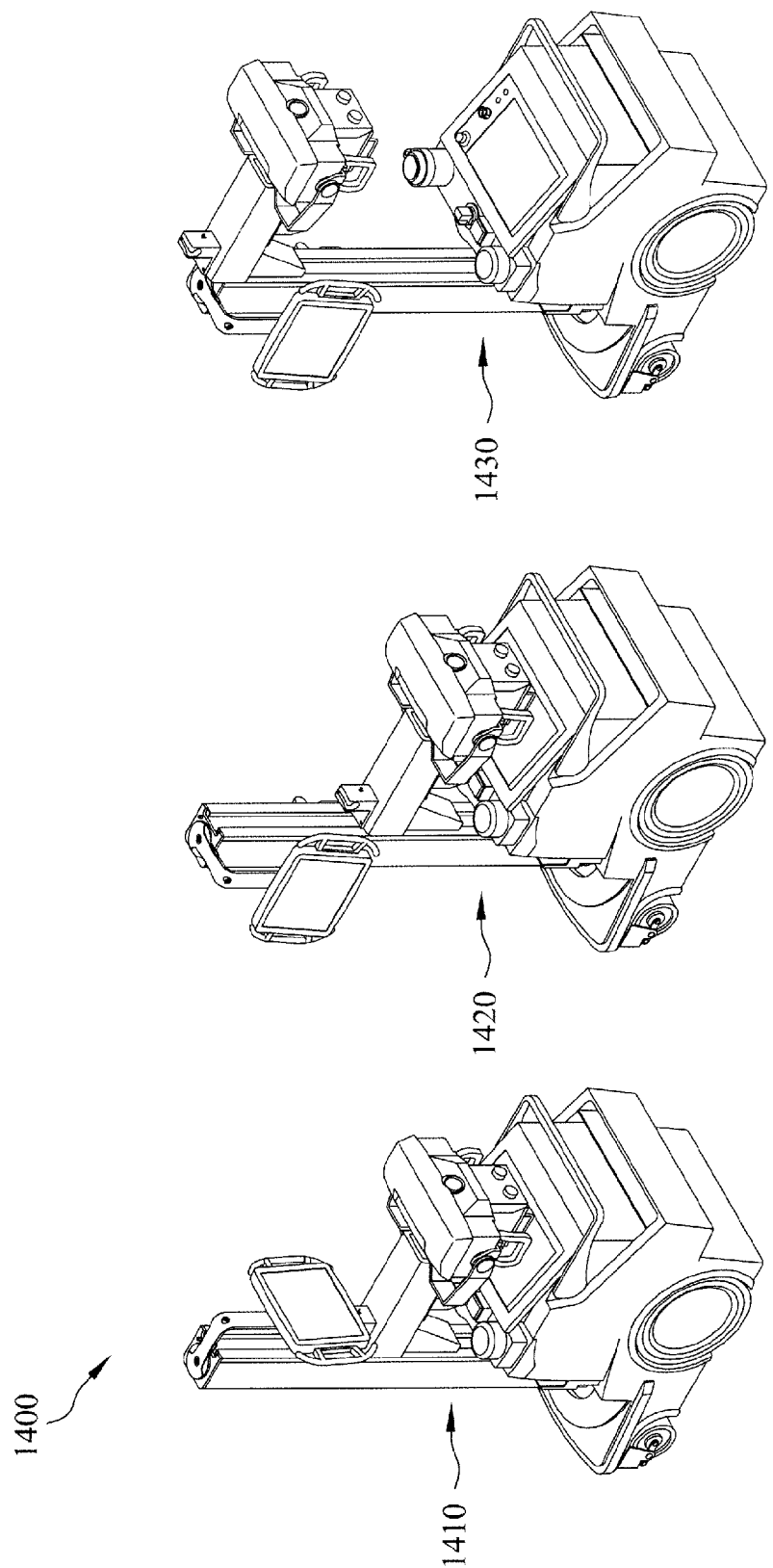
FIG. 14 illustrates a side view of a plurality of arm and monitor positions, in accordance with one embodiment of the present invention.

FIG. 14 illustrates a side view of a plurality of arm and monitor positions 1400, in accordance with one embodiment of the present invention.

The arm and monitor positions 1400 may include a transport mode position 1410, a monitor rotated 90 degree position 1420 and a DR fully-raised arm 1430 position.

The Monitor Arm is sized to permit full vertical range of the mobile DR Machine Arm. The Monitor Dock & Lock Device is designed such that it is not taller than the X-Ray Beam Source. The cables connecting the main computer to the Articulating Monitor are concealed within the structure of the Monitor Arm.

Figure 15:
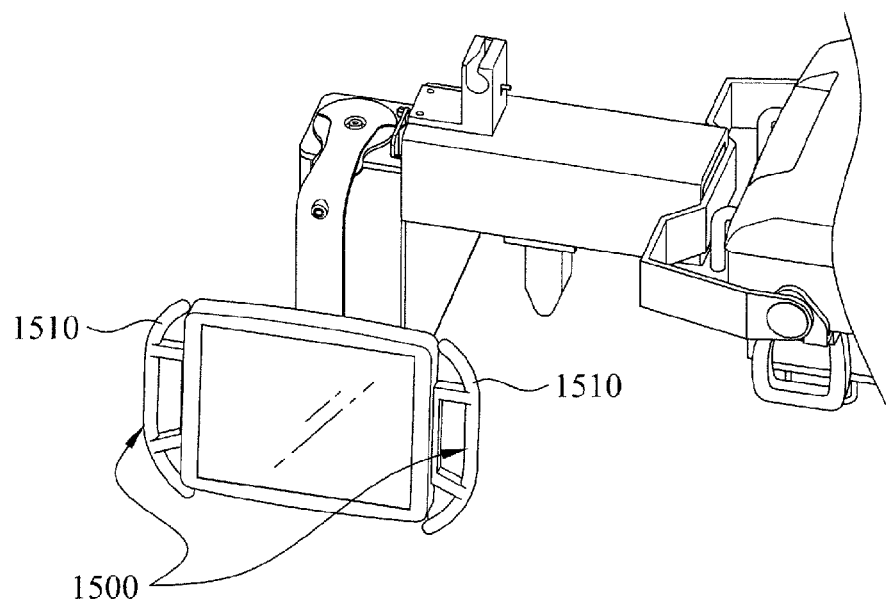
FIG. 15 illustrates a front view of a pair of handle grips, in accordance with one embodiment of the present invention.

FIG. 15 illustrates a front view of a pair of handle grips 1500, in accordance with one embodiment of the present invention.

The pair of handle grips 1500 may include a pair of bumpers 1510 disposed over the pair of handle grips 1500 to provide comfort to a person grasping the pair of handle grips 1500.

The images also show optional Handle Grips which also serve as bumper guards. The shape of the bumper guards protects against collision damage between the DR Arm and the Articulating Monitor.

Figure 16:
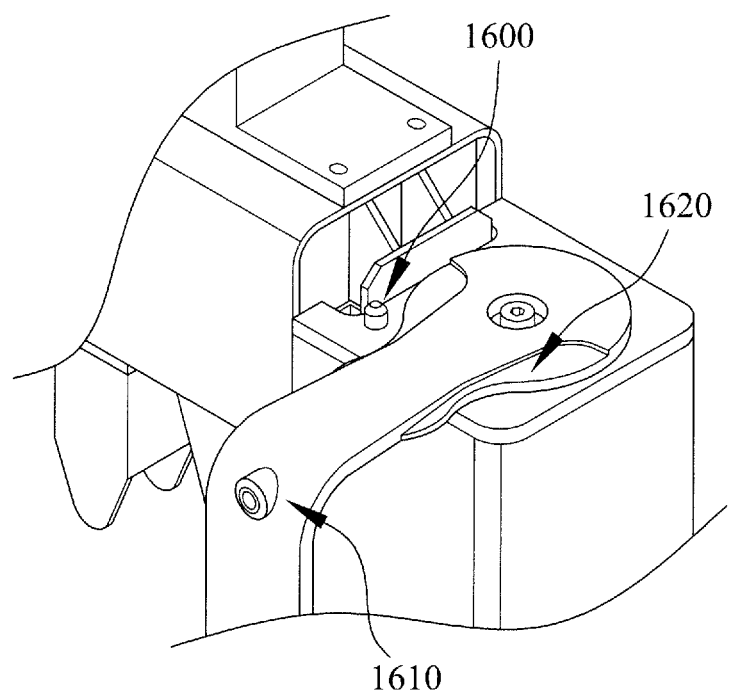
FIG. 16 illustrates a top view of a bumper stop and an LED indicator, in accordance with one embodiment of the present invention.

FIG. 16 illustrates a top view of a bumper stop 1600 and an LED indicator 1610, in accordance with one embodiment of the present invention.

The bumper stop 1600 may also include a bumper 1620.

A Bumper Stop protrudes from the top of the Column. This stop ends the rotational travel range of the Monitor Arm at 270 degrees from the docking position. There is also a plastic Bumper that is integrated to the Monitor Arm. This prevents damage to the Monitor Arm when the DR Arm is fully raised and the Monitor Arm is rotated back toward the dock position.

Figure 17:
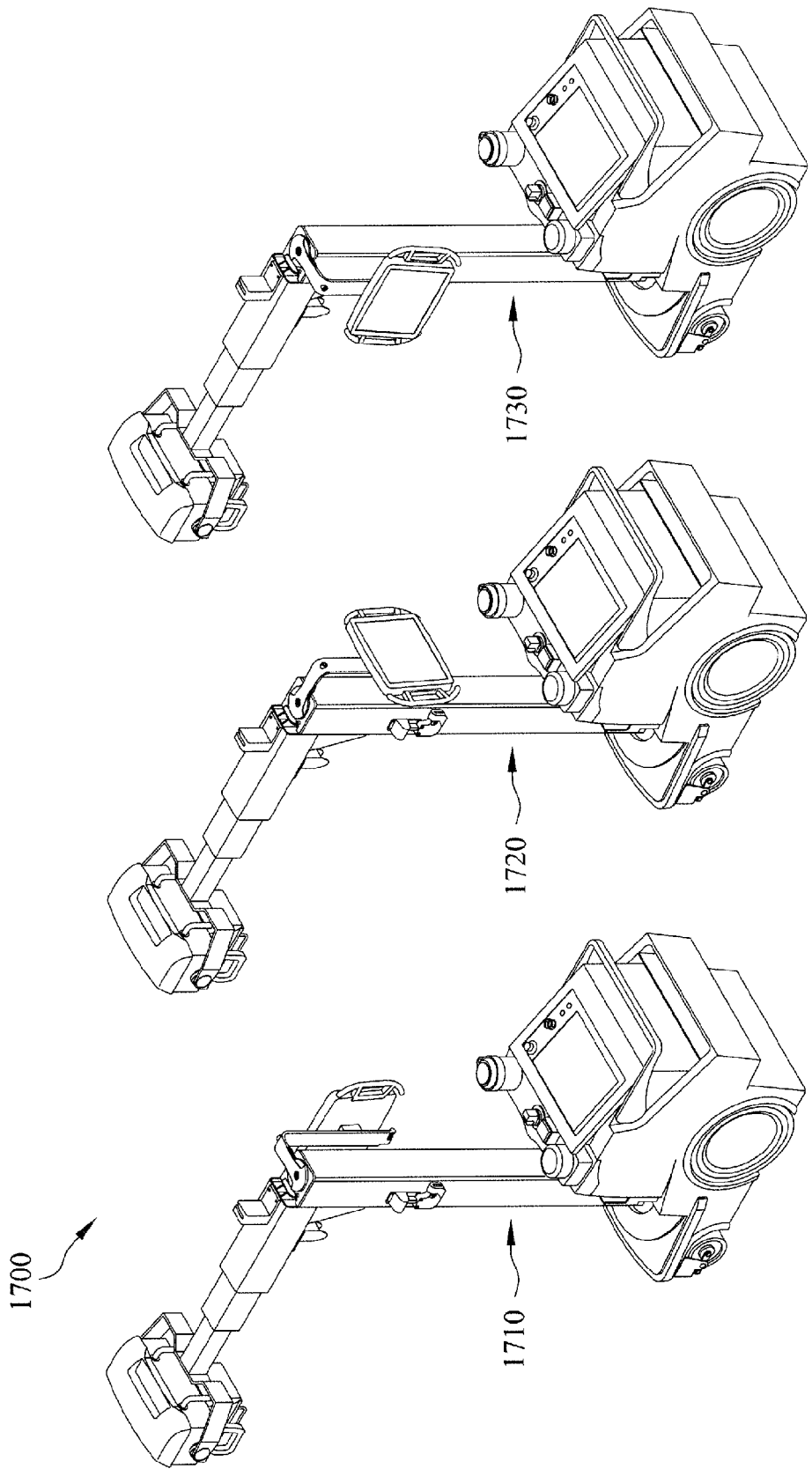
FIG. 17 illustrates a side view of a plurality of articulating monitor arm positions, in accordance with one embodiment of the present invention.

FIG. 17 illustrates a side view of a plurality of articulating monitor arm positions 1700, in accordance with one embodiment of the present invention.

The articulating monitor arm positions 1700 may include a first arm position 1710, a second arm position 1720 and a third arm position 1730.

The images below show some "Diagnostic Use Mode" positions. The Articulating Monitor Arm rotates with the DR Machine Column as it is rotated and is additionally free to rotate about the top of the Column.

While the present invention has been related in terms of the foregoing embodiments, those skilled in the art will recognize that the invention is not limited to the embodiments described. The present invention may be practiced with modification and alteration within the spirit and scope of the appended claims. Thus, the description is to be regarded as illustrative instead of restrictive on the present invention.

What is claimed is:

1. An articulating display and control monitor device utilized by a mobile radiographic machine, comprising:
a display monitor coupled to a monitor arm, the monitor arm coupled to a rotational pivot device, the rotational pivot device coupled to a top of a mobile radiographic machine column, the display monitor rotates about a vertical axis extending from the mobile radiographic machine thereby allowing the display monitor to rotate around the mobile radiographic machine column, the display monitor is utilized by the mobile radiographic machine only when the monitor arm is undocked and the monitor arm undocks only when the articulating display and control monitor device is undocked; and
a video device with a selected one of a video camera and a web cam, the video device provides a video stream from an area in front of the mobile radiographic machine to assist a user transporting the mobile radiographic machine as the video stream is displayed on the display monitor, the display monitor utilizes a video streaming drive mode only when the monitor arm is docked, the display monitor is utilized in conjunction with the articulating display and control monitor device only when the monitor arm is undocked, the monitor arm docks only when the articulating display and control monitor device is docked, the monitor arm is undocked unless until the mobile radiographic machine is already docked and the mobile radiographic machine monitor cannot be undocked until the monitor arm is undocked.

2. The articulating display and control monitor device according to claim 1, wherein the display monitor is in a docked and locked position when the articulating display and control monitor device is transported.

3. The articulating display and control monitor device according to claim 1, wherein the display monitor rotates around the mobile radiographic machine column 270 degrees.

4. The articulating display and control monitor device according to claim 3, wherein the display monitor is stopped by one or more stops protruding from the top of the mobile radiographic machine column when the display monitor rotates around the mobile radiographic machine column.

5. The articulating display and control monitor device according to claim 1, wherein the display monitor includes a pair of handle grip bumpers.

6. The articulating display and control monitor device according to claim 1, wherein the display monitor is capable of being pivoted, swiveled, tilted, moved vertically and moved horizontally.

7. The articulating display and control monitor device according to claim 1, wherein the display monitor is a touch screen monitor.

8. The articulating display and control monitor device according to claim 1, wherein the selected one of a video camera and a web cam is capable of being tilted and panned.

9. The articulating display and control monitor device according to claim 1, wherein the display monitor is in a docked rear facing position when the video stream is displayed on the display monitor.

10. The articulating display and control monitor device according to claim 9, wherein the display monitor is held in a docked rear facing position with a lock latch.

11. A mobile radiographic machine, comprising:
a base mobile radiographic machine;
a display monitor coupled to a monitor arm, the monitor arm coupled to a rotational pivot device, the rotational pivot device coupled to a top of a mobile radiographic machine column, the display monitor rotates about a vertical axis extending from the mobile radiographic machine thereby allowing the display monitor to rotate around the mobile radiographic machine column, the display monitor is utilized by the mobile radiographic machine only when the monitor arm is undocked and the monitor arm undocks only when the articulating display and control monitor device is undocked; and
a video device with a selected one of a video camera and a web cam, the video device provides a video stream from an area in front of the mobile radiographic machine to assist a user transporting the mobile radiographic machine as the video stream is displayed on the display monitor, the display monitor utilizes a video streaming drive mode only when the monitor arm is docked, the display monitor is utilized in conjunction with the articulating display and control monitor device only when the monitor arm is undocked, the monitor arm docks only when the articulating display and control monitor device is docked, the monitor arm is undocked unless until the mobile radiographic machine is already docked and the mobile radiographic machine monitor cannot be undocked until the monitor arm is undocked.

12. The articulating display and control monitor device according to claim 11, wherein the display monitor is in a docked and locked position when the articulating display and control monitor device is transported.

13. The articulating display and control monitor device according to claim 11, wherein the display monitor rotates around the mobile radiographic machine column 270 degrees.

14. The articulating display and control monitor device according to claim 13, wherein the display monitor is stopped by one or more stops protruding from the top of the mobile radiographic machine column when the display monitor rotates around the mobile radiographic machine column.

15. The articulating display and control monitor device according to claim 11, wherein the display monitor includes a pair of handle grip bumpers.

16. The articulating display and control monitor device according to claim 11, wherein the display monitor is capable of being pivoted, swiveled, tilted, moved vertically and moved horizontally.

17. The articulating display and control monitor device according to claim 11, wherein the display monitor is a touch screen monitor.

18. The articulating display and control monitor device according to claim 11, wherein the selected one of a video camera and a web cam is capable of being tilted and panned.

19. The articulating display and control monitor device according to claim 11, wherein the display monitor is in a docked rear facing position when the video stream is displayed on the display monitor.

20. The articulating display and control monitor device according to claim 19, wherein the display monitor is held in a docked rear facing position with a lock latch.

* * * * *